United States Patent [19]
Kennedy

[11] Patent Number: 6,150,361
[45] Date of Patent: Nov. 21, 2000

[54] TRIAZINEONE COMPOUNDS FOR TREATING DISEASES DUE TO SARCOSYSTIS, NEOSPORA AND TOXOPLASMA

[75] Inventor: Thomas J. Kennedy, Mission, Kans.

[73] Assignee: Bayer Corporation, Pittsburgh, Pa.

[21] Appl. No.: 09/218,323

[22] Filed: Dec. 22, 1998

[51] Int. Cl.$^7$ ...................................................... A61K 31/53

[52] U.S. Cl. ............................................ 514/241; 514/242

[58] Field of Search ...................................... 514/241, 242

[56] References Cited

U.S. PATENT DOCUMENTS

| | | | |
|---|---|---|---|
| 4,219,552 | 8/1980 | Haberkorn et al. | 424/249 |
| 4,933,341 | 6/1990 | Lindner et al. | 514/241 |
| 5,883,095 | 3/1999 | Granstrom et al. | 514/242 |

FOREIGN PATENT DOCUMENTS

| | | |
|---|---|---|
| 198 24 483 | 12/1999 | Germany . |
| 98/43644 | 10/1998 | WIPO . |
| 00/19964 | 4/2000 | WIPO . |

OTHER PUBLICATIONS

D. S. Lindsay et al: "Examination of the Activities of 43 Chemotherapeutic Agents Against Neospora Caninum Tachyzoites in Cultured Cells", American Journal of Veterinary Research Vol. 55, No. 7, July 1994, pp. 976–981, XP002101367.

H. E. Krampitz et al "Experimental Treatment of Hepatozoon Infections With the Anticoccidial Agent Toltrazuril" *Journal of Veterinary Medicine* Series B–Zentralblatt Fuer Veterinaermedizin. Rene B, De, Paul Parey, Berlin, vol. 35 No. 2, (month unavailable) 1988, pp. 131–137, XP000882187.

*Primary Examiner*—Kevin E. Weddington
*Attorney, Agent, or Firm*—Joseph C. Gil; Godfried R. Akorli

[57] ABSTRACT

Disclosed herein are a methods of treating therapeutically, or metaphylactically infected animals susceptible to, or infected animal suffering from parasitic neurologic or abortigenic diseases such as Sarcocystidiae or Toxoplasmosis that are treatable with triazineone compound by administering thereto a pharmaceutically effective amount of ponazuril, including a single high dose therapeutic treatment.

19 Claims, No Drawings

TRIAZINEONE COMPOUNDS FOR TREATING DISEASES DUE TO SARCOSYSTIS, NEOSPORA AND TOXOPLASMA

BACKGROUND OF THE INVENTION

1. Field of the Invention

The present invention relates to triazineone compounds for treating animals infected with parasites that cause abortigenic or neurologic diseases. More specifically, the present invention relates the triazineone compounds that are useful in treating parasitic protozoa such as coccidia that cause abortigenic or neurologic diseases.

2. Brief Description of the Prior Art

Triazineone compounds such as triazinediones, e.g., diclazuril compounds, and triazinetriones, e.g., toltrazuril compounds have been used in treating and protecting various mammals, insects and fish from diseases caused by a broad range of protozoa. See U.S. Pat. Nos.; 4,933,341; 4,935,423; 5,114,938; 5,141,938; 5,188,832, 5,196,562, 5,256,631 and 5,464,837. Protozoa sensitive to these compounds include parasites, which infect the intestines of birds, mammals and insects and manifest as diarrhea, wasting, nausea and vomiting. Generally, the mode of action of the triazineones is to attack the intermediate parasite stages found in the gut and intestinal wall cells, causing the endoplasmic reticulum, the perinuclear space and the mitochondria of the parasite to swell. This purportedly disturbs the ability for nuclear divisions causing the shizonts and microgamonts to remain small forming only a few merozoites and microgametes respectively. The end result is reported to be the loss of the ability of these latter stages of the parasites to penetrate new mammalian cells, effectively halting the replication of the parasite in the host.

Of particular concern here are certain protozoa suspected of causing neurologic and/or abortigenic diseases of animals since the 1970's. Successful isolation and in vitro cultivation of some of these protozoa proved to be difficult. For example successful isolation from the brain or cerebral spinal fluid were not accomplished until the late 1980s. Once it was determined that neurologic diseases could be produced by parasites infecting the brain and abortigenic diseases could be produced infecting the fetus, there was a need for effective anti-protozoa drugs which could cross the blood-brain barrier and the placental barrier without producing deleterious side effects. Very few drugs are able to pass the blood-brain barrier or the placental barrier of animals. However, many of the art-known drugs that can to cross the blood-brain barrier and/or the placental barrier to effectively treat parasitic infections of the brain have detrimental side effects such that they cannot be used without great risk. Therefore, there have been no effective drugs approved to date which provide an effective treatment for such neurologic or abortigenic diseases. The following is a brief description of the parasitic diseases.

Equine Protozal Myeloencephalitis (EPM) is a neurologic disease of horses, with a predilection for young horses undergoing stress (e.g., thoroughbred race horses and purebred performance horses), and is thus a disease with significant monetary impact for the horse industry. EPM, first recognized as a disease in the 1970's, was not cultured from a horse with EPM and given the name *Sarcocystis neurona* until 1991. In 1997, a Neospora spp., now named *Neospora hugesi*, was isolated from the brain of a horse with EPM. Accordingly, it is now proposed that EPM may be caused by this newly recognized organism alone, by *Sarcocystis neurona* alone or the combination of the two. EPM most often results in asymmetric incoordination (ataxia), weakness, and spasticity. The disease can mimic almost any neurologic condition. It can occur as a peracute or chronic condition. The chronic form is often insidious at onset, difficult to diagnose until late in the course of the disease, and can result in death. In the mildest cases, the only clinical sign may be ill-defined pelvic limb lameness or a minor respiratory noise. In the most severe cases, horses are unable to swallow or stand. It is now known that in the most severe cases, the parasite, e.g., *S. neurona* infects the brain and produces significant damage therein. The clinical signs of EPM are caused by direct neuronal (brain and spinal cord) damage by the parasites as well as brain damage resulting from infiltration of inflammatory cells, edema, and neuronal death associated with merozoites and meronts in the central nervous system (CNS). Currently, there is no approved effective treatment or prophylaxis for the control of EPM. The human drug trimethoprim-sulfonamide combination has been used. However, treatment is expensive and requires an extensive number of repeated doses.

Another coccidian parasite, *Toxoplasma gondii*, has been known for some time and was first isolated from the intestines and muscle tissue of cats. The definitive host for this parasite is the cat that can harbor the organism for long periods of time spreading oocysts to other animals including bovines, ovines swine and humans. Infection of sheep, cattle and humans has been associated with abortion and congenitally acquired disorders, which primarily affect the central nervous system. It has also recently been associated with abortion and malformation in kittens born to infected queens that had been seronegative prior to infection during pregnancy. Non-feline hosts such as bovines, ovines swine and humans do not produce oocysts but develop and may suffer from invasion of muscle and brain by tachyzoites and bradyzoites which produce the clinical signs of disease—neurological symptoms and abortion with fetal defects. It has been reported that 60% of cats are serologically positive to *T. gondii*. Once again, there is no approved treatment or prophylactic for toxoplasmosis.

Yet another coccidia parasite, *Neospora caninum*, produces both a neurologic and abortigenic disease in animals. It was first isolated from dogs in 1988. It was previously confused with *Toxoplasma gondii*. The disease caused by this parasite occurs most severely in transplacentally infected puppies and is characterized by progressive ascending paralysis in the puppies, particularly of the hind limbs; polymyositis and hepatitis may also occur. This disease has more recently been recognized as a major cause of abortion and neurologically-associated limb defects in newborn calves. Microscopic lesions of non-suppurative encephalitis and myocarditis in aborted fetuses may be seen in the brain, spinal cord and heart. A definitive host for *Neospora caninum* has recently been identified to be the dog. At this time there is no approved treatment or prophylaxis for either *Neospora caninum* of dogs or bovines or *Neospora hugesi* of horses.

Art-known references, including the above-cited references do not suggest or teach the use of triazineone compounds such as Toltrazuril or Toltrazuril Sulfone (recently renamed "Ponazuril") in treating animals infected with coccidia or, more specifically, of the family Sarcocystidae causing abortigenic or neurologic diseases without causing intolerable side effects. There is, therefore, a need for an improved and safe treatment for animals afflicted with parasitic diseases manifesting as neurologic or abortigenic diseases.

SUMMARY OF THE INVENTION

1. In accordance with the foregoing, the present invention encompasses an improved method of therapeutically treating a diseased animal suffering from a parasitic neurologic or abortigenic disease that is susceptible to being treated with a triazineone compound, comprising administering to the animal a pharmaceutically effective amount of the compound, the improvement comprising the triazineone compound which is ponazuril.

The term "pharmaceutically-effective amount" as used herein means that the amount of triazineone being administered is high enough to inhibit the in vivo or in vitro growth of the parasitic protozoa, typically coccidia which, produce neurological disease and/or abortions. The pharmaceutically-effective amount controls the parasites in the infected tissues; consequently, the animal's health improves.

Further, the present invention encompasses a method of metaphylactically treating an animal infected with a parasite that can cause a neurologic or abortigenic disease, that is susceptible to being treated with ponazuril. The metapylactic treatment comprises administering to the animal the ponazuril using a metaphylactically-effective regimen. By the term "metaphylactically-effective regimen" is meant administering scheduled intermittent doses of triazineone compound for a prolonged period until said animal overcomes the invading parasites by, say, developing a protective immune response or otherwise clearing the parasite. Typically, the regimen is such as would effectively control the parasites and prevent clinical signs of disease. The metaphylactically-effective dose can also be administered for a prolonged period up to five years or the lifetime of the animal, especially in instance when the parasite is difficult to control.

Also, the present invention encompasses a single high dose treatment of the animals. This method comprises administering to the animals a single high dose of a pharmaceutically effective amount of ponazuril to a diseased animal suffering from a parasitic neurologic or abortigenic disease that is susceptible to being treated with a triazineone. By the term "single high dose" is meant an amount that is administered only once. This amount is significantly higher than the dose amount employed in the therapeutic or metapylactic treatment; is effective in controlling the disease-causing parasites, and as such would not result in detrimental effects such as toxicity. The single high dose of ponazuril is accordingly greater than 10 mg/Kg. This and other aspects of the invention are described more fully hereunder.

DETAILED DESCRIPTION OF THE INVENTION

As set forth above, the present invention relates to a method of treating a infected or diseased animal suffering from a parasitic disease that manifests as neurologic or abortigenic disease that is susceptible to being treated with triazineone compound, comprising, administering thereto a pharmaceutically effective amount of ponazuril. Illustrative but non-limiting examples of the animals can be equines, bovines, felines, canines, swine, ovines, birds, insects and humans. The parasites infecting or causing disease are coccidia of the Family Sarcocystidae that can that can manifest as neurologic or abortigenic diseases. Illustrative but non-limiting examples thereof can be selected from the group consisting of Sarcocystis spp., Neospora spp. and Toxoplasma spp. The Sarcocystidae are typically selected from the group consisting of S. neurona, N. hugesi, N. caninum and T gondii. The protozoan infections or diseases include but are not limited to EPM, Neosporosis, and Toxoplasmosis.

In the practice of the invention, treatment of the parasitic infections or diseases caused by the protozoa described herein results in the alleviation of the symptoms of the neurologic and abortigenic diseases. Generally, the symptoms include lameness, ataxia, paralysis, abortion, weak newborns and other related disorders. For the therapeutic treatment, animals already suffering the above signs of disease are treated with the triazineone compound. Typically the duration of treatment is from about 28 days to 90 days and preferably from about 28 to 60 days. It is understood that for therapeutic treatment, the treatment regimen can be once a day, two or more times a day, once every other day or even once per week, depending on factors such as the severity of the disease and the type of disease-producing parasite. In some cases, however, the treatment regimen can last indefinitely, sometimes for the remaining life of the animal. The latter treatment would be required in the case of infection of an animal with a more resistant strain of parasite. However, the treatment can be extended for longer periods of time as necessary until the signs of disease are eliminated. The preferred treatment is once, daily for about 28 days.

For the metaphylactic treatment, animals that are infected are treated to protect them against clinical manifestation of diseases. This treatment eventually results in the animals' acquisition of the ability to control the parasite, say, by the establishing an effective immune response to impart protection against future infections, without a need for further administration of ponazuril. The metaphylactic activity, in accordance with the invention, refers to the use of the triazineone compounds on a scheduled intermittent treatment regimen (metaphylactically-effective regimen) to control the protozoa, which may have infected the animal, since the previous treatment. Accordingly, the metaphylactically-effective regimen is administered to reduce their ability to cause disease by, say, killing them or reducing them in number. In essence, the metaphylactically effective regimen can be administered about once per month, over the lifetime of the animal or until an inherent clearance mechanism, e.g., an effective immune response, develops within the animal to protect it from future infections. The latter can occur within 5 years or less. As would be realized, the metaphylactic treatment is based on the recognition that when animals are infected with the protozoa described herein, they do not demonstrate clinical signs such as neurological signs or abortion until a significant time has passed (e.g., 2–6 months post infection). In contrast, the enteric protozoan infections manifest themselves shortly after infection. In accordance with this invention, the metaphylactic treatment prevents the parasite from establishing itself and causing a clinical disease. The treatment regimen is on an intermittent schedule of about once per month, once per two months or once per two weeks at a dose equivalent to about between 1.0 and 100 mg/Kg, preferably about 1.0 to 25 mg/Kg and more preferably about 2.5 to 10 mg/Kg. The high range would be required in particularly resistant cases (e.g., when an animal is infected with a resistant strain). The required dose level and duration of treatment are within the purview of one of ordinary skill in the art. A preferred treatment regimen for horses with EPM or bovines with Neosporosis is about 1.0 to 25 mg/Kg, and a more preferred range is about 2.5 to 10 mg/Kg of triazinetrione every 28 days.

For the single high dose treatment ponazuril is administered in pharmaceutically effective amounts that are greater than 10 mg/Kg and up to about 100 mg/Kg. It is a distinct feature of the invention the compounds of this invention can be non-toxic, thus they can be administered at high dose levels. The advantage of the high dose administration resides in the fact repeated doses are not required and that some triazineone compounds can cause detrimental side effects if administered at very high dose levels.

Without being bound to any particular theory of the invention, it believed that the unexpected success of the treatments described herein results from the ability of ponazuril to cross the blood-brain barrier or placental barrier. It is believed that the compounds of this invention easily cross the blood-brain barrier and, also, are able to penetrate the placenta and kill the protozoa in situ in the brain and cerebral spinal fluid/spinal cord. It has been a further been found that the compounds of this class are non-toxic and non-mutagenic even at the high doses necessary for the single high dose treatment regimen described herein.

Heretofore, no cost-effective, easily administered drugs have been available for effectively treating and protecting against these diseases without producing unacceptable side effects such as toxicity or mutagenicity in animals.

In the practice of the invention, ponazuril can be formulated in any convenient manner for administration to animals. Formulations suitable for oral administration, which is preferred herein, can be suspensions, tablets, capsules, gels, pastes, boluses, or preparations in the form of powders, granules, or pellets. The preferred orally administered formulation is in the form of a paste or a feed additive. Other modes of administration that can be employed include parenteral, topical, intramuscular, and intramucosal or by other routes known to those skilled in the art. Topical administration in the form of a pour-on is also preferred.

Typically, pharmaceutically acceptable carriers and auxiliaries are employed in the formulations. Examples thereof can be a thickening agents selected from the group consisting of: Carbopol, inorganic thickeners such as silicates, bentonites or colloidal silica and organic thickeners such as fatty alcohols or fatty acid esters and the wetting agent is selected from the group consisting of polyethylene glycol and sodium lauryl sulfate with Carbopols, more specifically, Carbopol 974P being the most preferred thickening agent for the paste formulation preferred herein. Also employed herein can be preservatives selected from the group consisting of parabens, alcohols and aldehydes. These may be liquid, solid, or gaseous materials, which are otherwise inert or medically acceptable and are compatible with the active ingredients.

Surprisingly, the pastes, according to the invention, are effective when used in treating the parasites. More specifically, it is surprising that the pastes of the present invention are effective in delivering the triazineones, particularly Toltrazuril, and Ponazuril to cross the blood-brain or placenta barrier and attack the parasites which have already invaded the brain or infected the fetus of a pregnant animals. As a matter convenience, there is provided herein a description of a specific embodiment of the pastes preferred herein and how it is prepared. A preferred paste, according to the present invention contains a micronized suspension of the triazinetrione (e.g., Ponazuril), propylene glycol, a thickening agent such as Carbopol, preservatives such as Methylparaben and Propylparaben, and water. It can be made by combining water, typically, purified water and Propylene Glycol, heating the combination to about 70° C., and adding the preservatives, at this temperature. The resulting mixture is cooled to room temperature after which Carbopol, preferably in the form of Carbopol 974P, is added. Finally the triazinetrione is added. After complete mixing, the pH is adjusted to approximately 6.0 with sodium hydroxide. The most preferable paste includes 15% w/w Ponazuril, 20% w/w Propylene Glycol, 0.5% w/w Carbopol 974P, 0.14% w/w Methylparaben, 0,02% w/w Propylparaben, 0.1% w/w sodium hydroxide with the remainder being purified water. Sweeteners including dextrose, sucrose, lactose, fructose, sorbitol, xylitol, artificial sweeteners and molasses may be added to improve palatability. Additionally, yeast or liver flavoring may be added for the same purpose.

The invention is further described by following illustrative but non-limiting examples.

EXAMPLES

Example 1

A pharmacokinetic study was conducted in horses comparing blood levels of Toltrazuril, Ponazuril and Toltrazuril Sulfoxide at various times post a single dose of Toltrazuril. All horses received a single dose of 10 mg/kg, which was administered orally as a suspension. Blood samples were drawn at the time of treatment (0) and at 0.25, 0.5, 1, 2, 4, 6, 12, 24, 48 and 72 hours post treatment. Results of the sampling are listed in Table 1. It was surprising to note that horses receiving Toltrazuril demonstrated relatively high levels of Ponazuril in their serum. Additionally, significant levels of Toltrazuril sulfoxide were found in the bloodstream. This was an indication that Ponazuril, alone, would produce acceptable blood levels that are envisioned to pass the blood-brain barrier, a characteristic required to treat neurological diseases such as those caused by *Sarcocystis neurona*, *Toxoplasma gondii*, *Neospora caninum* and *Neospora heugesi*.

TABLE 1

Pharmacokinetics of a Single Dose of Toltrazuril in Horses

| D | Compound Measured | Concentration in mg/l of Blood | | | | | |
|---|---|---|---|---|---|---|---|
| | | 0 | 0.25 | 0.5 | 1 | 2 | 4 |
| A | Toltrazuril | | 0.027 | 0.773 | 2.863 | 4.511 | 3.119 |
| | Toltrazuril-Sulfoxide | | <0.01 | 0.077 | 0.070 | 0.159 | 0.142 |
| | Ponazuril | | 0.010 | 0.089 | 0.088 | 0.171 | 0.110 |
| B | Toltrazuril | | 0.061 | 0.393 | 2.617 | 4.296 | 6.820 |
| | Toltrazuril Sulfoxide | | <0.01 | 0.025 | 0.047 | 0.083 | 0.157 |
| | Ponazuril | | <0.01 | 0.029 | 0.036 | 0.040 | 0.050 |
| C | Toltrazuril | | 0.061 | 0.560 | 3.286 | 5.788 | 9.079 |
| | Toltrazuril Sulfoxide | | <0.01 | 0.024 | 0.041 | 0.097 | 0.218 |
| | Ponazuril | | <0.01 | 0.013 | 0.019 | 0.026 | 0.032 |
| D | Toltrazuril | | 0.017 | 0.295 | 3.286 | 2.165 | 3.328 |
| | Toltrazuril Sulfoxide | | <0.01 | 0.027 | 0.039 | 0.058 | 0.100 |
| | Ponazuril | | <0.01 | 0.011 | 0.021 | 0.024 | 0.029 |
| E | Toltrazuril | | <0.01 | 0.039 | 1.146 | 3.175 | 8.410 |
| | Toltrazuril Sulfoxide | | <0.01 | <0.01 | 0.021 | 0.064 | 0.194 |
| | Ponazuril | | <0.01 | <0.01 | 0.017 | 0.015 | 0.044 |
| F | Toltrazuril | | 0.110 | 0.428 | 1.741 | — | 8.144 |
| | Toltrazuril Sulfoxide | | <0.01 | 0.026 | 0.044 | — | 0.183 |
| | Ponazuril | | <0.01 | 0.012 | <0.01 | — | 0.041 |

| D | Compound Measured | Concentration in mg/l of Blood | | | | |
|---|---|---|---|---|---|---|
| | | 6 | 12 | 24 | 48 | 72 |
| A | Toltrazuril | 5.149 | 5.066 | 6.434 | 7.607 | 6.653 |
| | Toltrazuril-Sulfoxide | 0.167 | 0.230 | 0.407 | 0.732 | 0.592 |
| | Ponazuril | 0.108 | 0.170 | 0.324 | 1.622 | 1.933 |
| B | Toltrazuril | 11.474 | 11.670 | 11.690 | 6.677 | 5.058 |
| | Toltrazuril Sulfoxide | 0.320 | 0.451 | 0.566 | 0.454 | 0.346 |
| | Ponazuril | 0.131 | 0.254 | 0.255 | 0.831 | 0.880 |
| C | Toltrazuril | 14.202 | 13.751 | — | 9.758 | 7.633 |
| | Toltrazuril Sulfoxide | 0.280 | 0.436 | — | 0.477 | 0.377 |
| | Ponazuril | 0.061 | 0.135 | — | 0.540 | 0.642 |
| D | Toltrazuril | 3.816 | 10.544 | 7.236 | 8.234 | |
| | Toltrazuril Sulfoxide | 0.133 | 0.668 | 0.461 | 0.749 | — |
| | Ponazuril | 0.030 | 1.651 | 0.315 | 0.986 | — |
| E | Toltrazuril | 11.335 | 12.032 | 8.694 | 6.869 | — |
| | Toltrazuril Sulfoxide | 0.259 | 0.430 | 0.481 | 0.741 | — |
| | Ponazuril | 0.074 | 0.268 | 0.231 | 0.501 | — |
| F | Toltrazuril | 10.966 | 6.660 | 10.224 | 7.096 | — |
| | Toltrazuril Sulfoxide | 0.245 | 0.453 | 0.633 | 0.642 | — |
| | Ponazuril | 0.061 | 0.725 | 0.192 | 0.532 | — |

Example 2

Ponazuril, 1-methyl-3-[4-p-[trifluoromethyl)sulfonylphenoxy]-m-tolyl]-s-triazine-2,4,6 (1H,3H,5H)-trione, a representative Triazinetrione, was formulated into a paste for administration to horses. The components listed in Table 2 were used in preparing formulations as follows.

TABLE 2

Components of Ponazuril Horse Paste

| Ingredient | Theoretical Amount | Actual Amount % w/w |
|---|---|---|
| Ponazuril - Micronized | 22.5 Kg | 15.0 |
| Propylene Glycol | 30.0 Kg | 20.0 |
| Carbopol 974P | 0.750 Kg | 0.5 |
| Methylparaben, NF | 0.210 Kg | 0.14 |
| Propylparaben, NF | 0.030 Kg | 0.02 |
| Sodium Hydroxide, NF | 0.150 Kg | 0.10 |
| Purified Water | 96.365 Kg | 64.24 |

The formulations were prepared using process (A) and (B) as follows. The first process (A) comprised: 1) Mixing a portion of the water with the Propylene Glycol; 2) adding the preservatives (Methylparaben and Propylparaben; 3) slowly adding the Carbopol 974P until an even suspension was prepared; 4) adding the Ponazuril in a micronized form; 5) adding the Sodium Hydroxide to bring the suspension to a pH of approximately 6.0; and 6) adding the remainder of the water to QS to volume. The final suspension was in the form of a paste, which can be delivered orally to a horse.

The second process (B) comprised: 1) Mixing a portion of the water with the Propylene Glycol; 2) heating to 70° C.; 3) adding the preservatives (Methylparaben and Propylparaben while holding the solution at 70° C.; 4) cooling the solution to room temperature; 5) slowly adding the Carbopol 974P until an even suspension was prepared; 6) adding the Ponazuril in a micronized form; 7) adding the Sodium Hydroxide to bring the suspension to a pH of approximately 6.0; and 8) adding the remainder of the water to QS to volume. The final suspension was also in the form of a paste, which can be delivered orally to a horse.

The resulting pastes were administered to horses and found to be palatable and well accepted.

Example 3

Ponazuril, 1-methyl-3-[4-p-[trifluoromethyl)sulfonylphenoxy]-m-tolyl]-s-triazine-2,4,6 (1H,3H,5H)-trione, a representative Triazinetrione, was tested for its ability to treat horses already demonstrating signs of Equine Protozoal Myoencephalitis (EPM). The compound was formulated into a paste using Ponazuril as a 15% active ingredient (a.i.) as described in EXAMPLE 1. It was administered to horses already diagnosed with EPM once a day for 28 days at a dose rate between 2.5 mg/Kg and 10 mg/Kg.

Naturally occurring clinical cases of EPM were well characterized by signalment and laboratory diagnosis. The diagnosis used for incorporation of EPM-positive horses into this trial was as follows: Confirmed asymmetrical neurological deficit as determined by a standardized neurological examination, to include radiography, indicative of EPM; Positive Western Blot for *Sarcocystis neurona* IgG; Red Blood Cell count below 500 cells/mL; CSF indices—Total Protein<90, IgG index>0.3. AQ quotient<2.2.

Additional requirements were that the horses were not suffering from diseases other than EPM. Therefore, they had to meet the following criteria: Negative CSF (<1:4) for EHV-1; Normal serum values for Vitamin E (.2.0 μg/mL); Lack of seizure disorders; Lack of behavior disorders.

Diagnosed horses were randomly assigned to groups. Group 1 horses received the paste formulation daily at a dose rate of 5 mg/Kg whereas Group 2 horses received the paste formulation daily at a dose rate of 10 mg/Kg. The treatment dose was based on body weight. The horses were evaluated for a period of 90 days (approximately 60 days after discontinuation of treatment) in order to determine that treatment was indeed effective. The response to treatment was scored using the following system:

1) 0=complete success-clinically normal with a negative CSF; 2) 1=Deficit just detected at a normal gait; 3) 2=Deficit easily detected and exaggerated by backing, turning, swaying, jaw loin pressure and neck extension; 4) 3=Deficit very prominent on walking, Facial turning, loin pressure or neck extension; 5) 4=Stumbling, tripping and falling down spontaneously; 6) 5=Recumbent, unable to rise. An improvement of one (1) unit in the score was considered a significant improvement.

Results of this study are shown in Table 3. All (100%) of the horses in the 10 mg/Kg group which were treated for 28 days showed a significant improvement in clinical score by day 90 post start of treatment with Ponazuril (day 0). Eight of nine (88.9%) horses treated with the 5 mg/Kg dose demonstrated acceptable improvement. When adding all of the scores for each group for each treatment day, a total score is obtained. The improvement in total scores demonstrated by both Group 1 and Group 2 horses is approximately equivalent. It is thus concluded that Ponazuril at either a 5 mg/Kg or 10 mg/Kg is effective for the active treatment of EPM in horses.

TABLE 3

Response of EPM-Infected Horses to Treatment with Toltrazuril Sulfone

| Horse ID | 5 mg/Kg Dose | | | 10 mg/Kg Dose | | |
|---|---|---|---|---|---|---|
| | Day 0 | Day 28 | Day 90 | Day 0 | Day 28 | Day 90 |
| A | 2 | 1 | 2 | | | |
| B | 2 | 1 | 1 | | | |
| C | | | | 4 | 2 | 1 |
| D | | | | 3 | 2 | 0 |
| E | | | | 2 | 2 | 1 |
| F | 3 | 2 | 0 | | | |
| G | | | | 2 | 1 | 1 |
| H | | | | 2 | 2 | 1 |
| I | 2 | 1 | 0 | | | |
| J | 2 | 0 | 0 | | | |
| K | | | | 3 | 0 | 0 |
| L | 2 | 3 | 3 | | | |
| M | 2 | 2 | 0 | | | |
| N | 2 | 2 | 0 | | | |
| O | 3 | 3 | 2 | | | |
| TOTAL | 17 | 13 | 6 | 19 | 15 | 4 |

Example 4

In order to determine the scope of protection provided by Ponazuril, in vitro testing was conducted. The following strains of parasites were evaluated for their sensitivity to this compound: Strain SN3 of *Sarcocystis neurona;* strain SF1 of *Sarcocystis falcatula;* strain RH of *Toxoplasma gondii;* and the NC-1 strain of *Neospora caninum.* Ponazuril was tested at 2 concentrations (1 µg/mL and 10 µg/mL).

Bovine turbinate (BT) cells were used for all in vitro studies. Cells were grown to confluency in 25 cm² flasks in RMPI 1640 media supplemented with 10% v/v fetal bovine serum (FBS), 100 Units penicillin (G/mL), 100 mg streptomycin/mL and $5 \times 10^{-2}$ mM 2-mercpatoethanol. After cell confluence was obtained, cells were maintained in the same media with reduced FBS (2% v/v). Cell cultures were incubated at 37 C. in a humidified atmosphere containing 5% carbon dioxide and 95% air.

For growth of parasites, BT cell monolayers were infected with parasites and examined with an inverted microscope for the development of lesions (cytopathic effect, "CPE") or the presence of many extracellular merozoites. Once lesions were observed, or many extracellular parasites were present, the monolayer was scraped with the tip of a 5 mL pipette and 1 to 3 drops of the merozoite-containing fluid was transferred to two flasks of fresh BT cells. Merozoites of *S. neurona* and *S. falcatula* were passaged in this manner every 5 to 10 days while the tachyzoites of *T. gondii* and *N. caninum* were passaged every 3 to 4 days.

The assay used to determine the effectiveness of Ponazuril was the Microtiter Monolayer Disruption Assay (MMDA). This assay was used to determine if the parasites or compound were toxic for BT cells. Flat bottomed 96-well microtiter plates were inoculated with BT cells and the resulting monolayers were used to determine the effects of Toltrazuril and Ponazuril on merozoite production as measured by CPE (plaque formation). Monolayers were inoculated with parasites (*S. neurona* or *S. falcatula* at a count of 50,000/well, *T. gondii* at a level of 10,000/well, and *N. caninum* at 20,000/well. All wells were inoculated with the test compound 2 hours after infection. Untreated and uninfected monolayer wells served as parasite controls and uninfected agent treated BT cells served as toxicity controls.

Each treatment was examined in replicates of 6. Each well was visually monitored daily and the assay was stopped when 90–100% of the untreated merozoite infected cells had lysed (90–100% CPE). All wells of the plates were rinsed in Phosphate Buffered Saline (PBS) and fixed in 100% methanol for 5 minutes after which they were stained in crystal violet solution. Areas of merozoite induced destruction or BT cell death due to toxicity do not take up the crystal violet. An ELISA plate reader was used to quantitate the crystal violet incorporation and these data were used to determine the concentration of Ponazuril that inhibits destruction by 50% (Inhibitory Concentration$_{50}$ or IC$_{50}$). The data demonstrating inhibition are presented in Table 4. It is noted that as little as 1 µg/mL of Ponazuril provided 100% inhibition of cell destruction produced by *N. caninum, T. gondii* and *S. falcatula* whereas 10 µg/mL of Ponazuril was required to produce 100% inhibition of cell destruction by *S. neurona.* This indicates that triazineones such as Toltrazuril and Ponazuril would be efficacious for treatment of diseases caused by the Coccidia known to associated with neurological and abortigenic disease syndromes including diseases caused by *S. neurona, N. caninum, N. hugesi* and *T. gondii.* Additionally, Ponazuril was not toxic to the BT cells.

TABLE 4

In vitro Data on Ponazuril

Percent Inhibition of Cell Destruction

| Organism | 0.1 µg/mL | 1 µg/mL | 5.0 µg/mL | 10 µg/mL |
|---|---|---|---|---|
| Sarcocystis neurona | 0 | 40 | 90 | 100 |
| Sarcycystis falcatula | 61 | 100 | 100 | 100 |

| | 0.001 µg/mL | 0.01 µg/mL | 0.1 µg/mL | 1.0 µg/mL |
|---|---|---|---|---|
| Neospora caninum NC-1 | 3 | 13 | 100 | 100 |
| Toxoplasma gondii | 11 | 16 | 100 | 100 |

Example 5

This experiment was conducted in order to determine whether triazineones such as Toltrazuril can pass the blood-brain barrier. Normal horses were divided into three groups of three horses per group. Group 1 horses received Toltrazuril administered orally as a 5% suspension at a dose level of 2.5 mg/Kg. Group 2 horses received Toltrazuril administered orally as a 5% suspension at a dose level of 5.0 mg/Kg. Group 3 horses received Toltrazuril administered orally as a 5% suspension at a dose level of 7.5 mg/Kg. The dosing was repeated daily for 10 days. Blood samples were drawn at 48, 96 and 240 hours and the concentration of Toltrazuril, Toltrazuril sulfoxide and Ponazuril in the serum was measured. Ten days after the start of the treatment (Day 10), a sample of cerebral spinal fluid was removed from each horse and the concentrations of Toltrazuril, Toltrazuril Sulfoxide and Ponazuril were again measured in these samples. The concentrations of Toltrazuril, Toltrazuril Sulfoxide and Ponazuril in the serum and cerebral spinal fluid are reported in TABLES 5a and 5b. Concentration of Ponazuril in the blood and cerebral spinal fluid after treatment of horses with Toltrazuril was significant, in that the concentration of Ponazruil in the cerebral spinal fluid after treatment of horses with Toltrazuril was essentially equivalent to the concentration of Toltrazuril itself. This is evidence that both Toltrazuril and Ponazuril effectively cross the blood-brain barrier and that Ponazuril crosses this barrier more effectively than does Toltrazuril. The data would suggest to one skilled in the art that the triazineones can also effectively cross the placental barrier.

TABLE 5a

Drug Levels after Repeated Doses of Toltrazuril in Horses

| Horse ID | 10 Day Dose (mg/Kg) | Toltrazuril Level 48 Hrs | 96 Hrs | 240 Hrs | Cerebral Spinal Fluid Day 10 |
|---|---|---|---|---|---|
| 1 | 2.5 | 4.49 | 9.85 | 15.29 | 0.23 |
| 2 | 2.5 | 4.0 | 9.09 | 9.60 | 0.06 |
| 3 | 2.5 | 11.6 | 13.1 | 15.21 | 0.15 |
| 4 | 5.0 | 7.28 | 14.17 | 24.92 | 0.19 |
| 5 | 5.0 | 9.18 | 14.03 | 16.54 | 0.12 |
| 6 | 5.0 | 9.26 | 18.19 | 17.59 | 0.26 |
| 7 | 7.5 | N/A | 27.74 | 30.08 | 0.50 |
| 8 | 7.5 | 9.90 | 19.55 | 24.15 | 0.21 |
| 9 | 7.5 | 10.46 | 18.47 | 23.53 | 0.45 |
| AVG | 2.5 mg/Kg Dose | 6.70 | 10.68 | 13.37 | 0.15 |
| AVG | 5.0 mg/Kg Dose | 8.57 | 15.46 | 19.68 | 0.19 |
| AVG | 7.5 mg/kg Dose | 10.18 | 21.92 | 25.95 | 0.39 |

TABLE 5b

Drug Levels after Repeated Doses of Toltrazuril in Horses

| Horse ID | 10 Day Dose (mg/Kg) | Ponazuril Level 48 Hrs | 96 Hrs | 240 Hrs | Cerebral Spinal Fluid Day 10 |
|---|---|---|---|---|---|
| 1 | 2.5 | 0.29 | 0.99 | 2.61 | 0.09 |
| 2 | 2.5 | 0.24 | 1.15 | 2.36 | 0.07 |
| 3 | 2.5 | 3.70 | 3.13 | 4.04 | 0.11 |
| 4 | 5.0 | 0.48 | 2.09 | 5.44 | 0.12 |
| 5 | 5.0 | 0.63 | 2.03 | 2.03 | 0.14 |
| 6 | 5.0 | 0.48 | 2.66 | 5.61 | 0.21 |
| 7 | 7.5 | 6.35 | 2.69 | 6.31 | 0.23 |
| 8 | 7.5 | 0.78 | 2.89 | 6.37 | 0.17 |
| 9 | 7.5 | 0.52 | 3.09 | 7.06 | 0.27 |
| AVG | 2.5 mg/Kg Dose | 1.41 | 1.76 | 3.00 | 0.09 |
| AVG | 5.0 mg/Kg Dose | 0.53 | 2.26 | 5.02 | 0.16 |
| AVG | 7.5 mg/Kg Dose | 2.55 | 2.89 | 6.58 | 0.22 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In an improved method of therapeutically treating a diseased animal suffering from a parasitic neurologic or abortigenic disease that is susceptible to being treated with a triazineone compound, comprising administering to the animal a pharmaceutically effective amount of the compound, the improvement comprising the triazineone compound which is ponazuril.

2. The method of claim 1 wherein the parasitic disease is caused by a Coccidia.

3. The method of claim 2 wherein the Coccidia is a member of the family Sarcocystidae.

4. The method of claim 3 wherein a member of the family Sarcocystidae is selected from the group consisting of Sarcocystis, Neospora and a Toxoplasma.

5. The method of claim 4 wherein the Sarcocystis is selected from the group consisting of Sarcocystis spp, the Neospora is selected from the group consisting of Neospora spp and the Toxoplasma is selected from the group consisting of Toxoplasma spp.

6. The method of claim 5 wherein the Sarcocystis spp is *Sarcocystis neurona,* the Neospora spp is *Neospora caninum* or *Neospora hugesi* and the Toxoplasma spp is *Toxoplasma gondii*.

7. The method of claim 4 wherein the Sarcocystis is *Sarcocystis neurona* causing Equine Protozoal Myeloncephylitis.

8. The method of claim 4 wherein the Neospora is *Neospora caninum* causing bovine or canine Neosporosis.

9. The method of claim 4 wherein the Toxoplasma is *Toxoplasma gondii*.

10. An improved method of metaphylactically treating animals infected with a parasite that is a causative agent for a neurologic or abortigenic disease that is susceptible to being treated with a triazineone compound, comprising administering thereto a metaphylactially-effective regimen of the triazineone compound, the improvement comprising the compound which is ponazuril.

11. The method of claim 1 or claim 10 wherein ponazuril is administered in two or more intermittent doses.

12. The method of claim 11 wherein the intermittent dose is administered in an amount of between 1.0 and 100 mg/Kg.

13. The method of claim 10 wherein ponazuril is administered until the animal has developed protective immunity.

14. The method of claim 1 or claim 10 wherein ponazuril is administered in an amount of between 2.5 mg/Kg and 10 mg/Kg.

15. The method of claim 1 wherein ponazuril is administered in a single high dose of greater than 10 mg/Kg.

16. The method of claim 1 wherein the ponazuril is administered in a regimen of 2.5 mg/Kg to 10 mg/Kg daily for a period of 28 days.

17. A therapeutic composition comprising (a) ponazuril in a pharmaceutically effective amount to treat a diseased animal that is susceptible thereto (b) a carrier, and (c) optionally, an auxiliary agent.

18. The composition of claim 17 which is in the form of a paste.

19. A method of treating equine protozoal myeloencephalitis EPM comprising administering to an equine suspected of suffering therefore a therapeutically effective amount of ponazuril.

* * * * *